United States Patent
Colic

(10) Patent No.: US 6,649,193 B1
(45) Date of Patent: Nov. 18, 2003

(54) PROPHYLACTIC THERAPEUTIC AND INDUSTRIAL ANTIOXIDANT COMPOSITIONS ENHANCED WITH STABILIZED ATOMIC HYDROGEN/FREE ELECTRONS AND METHODS TO PREPARE AND USE SUCH COMPOSITIONS

(75) Inventor: Miroslav Colic, Goleta, CA (US)

(73) Assignee: Henceforth Hibernia Inc., New York, NY (US)

( * ) Notice: Subject to any disclaimer, the term of this patent is extended or adjusted under 35 U.S.C. 154(b) by 0 days.

(21) Appl. No.: 09/591,194

(22) Filed: Jun. 9, 2000

Related U.S. Application Data

(60) Provisional application No. 60/138,913, filed on Jun. 1, 1999.

(51) Int. Cl.[7] .......................... A61K 9/00; A61K 9/127; A61K 31/714; A61K 33/00; A61K 41/00
(52) U.S. Cl. ................. 424/600; 424/400; 424/450; 424/684; 424/724; 424/DIG. 6; 514/52; 514/706; 514/730; 514/731; 514/732; 514/734; 514/736; 514/836; 514/970; 514/973
(58) Field of Search ................. 424/450, 600, 424/684, 724, DIG. 6, 400; 514/52, 970, 706, 730, 731, 732, 734, 736, 836, 973; 205/335, 337, 637

(56) References Cited

U.S. PATENT DOCUMENTS 5,736,027 A * 4/1998 Nakamura .................. 205/742

6,572,902 B2 * 6/2003 Abramowitz et al. ......... 426/66

FOREIGN PATENT DOCUMENTS

RU 2032354 * 4/1995

OTHER PUBLICATIONS

Derwent Abstract, accession No. 1995–391519, abstracting RU 2032354 (1995).*

Sasamori et al., "Stabilization of atomic hydrogen in both solution and crystal at room temperature," Science, vol. 265, 1994, pp. 1691–1693.*

* cited by examiner

Primary Examiner—John Pak
(74) Attorney, Agent, or Firm—Cohen, Pontani, Lieberman & Pavane

(57) ABSTRACT

The invention is directed to therapeutic antioxidant compositions which are enhanced by the stabilized atomic hydrogen; one of the most potent antioxidants. Such products can be used for prophylactic and therapeutic purposes in treatment of cancer, diabetes, autoimmune diseases, neurodegenerative diseases, cardiovascular diseases, skin diseases etc. The products described can be used independently or in combination with other drugs and treatment modalities. The products can also be used as dietetic products to aid in desired weigh loss. The described products can also be used to prevent oxidative and free radical damage to food and oxidation-prone industrial products. The invention also describes the methods to produce and stabilize atomic hydrogen and prepare and use such stabilized/encaged atomic hydrogen enhanced antioxidant compositions.

3 Claims, No Drawings

US 6,649,193 B1

PROPHYLACTIC THERAPEUTIC AND INDUSTRIAL ANTIOXIDANT COMPOSITIONS ENHANCED WITH STABILIZED ATOMIC HYDROGEN/FREE ELECTRONS AND METHODS TO PREPARE AND USE SUCH COMPOSITIONS

RELATED APPLICATIONS

This application claims priority from U.S. Provisional Patent Application Serial No. 60/138,913 which was filed on Jun. 1, 1999, the entire contents of which are incorporated herein by reference in its entirety.

BACKGROUND OF THE INVENTION

1. Field of the Invention

The invention provides prophylactic, therapeutic and industrial antioxidant compositions that are enhanced with stabilized atomic hydrogen/free electrons. The invention also provides methods to prepare and use such antioxidant compositions.

2. Description of the Related Art

Molecular oxygen is an essential substance for all aerobic organisms, including humans. Oxygen is involved in many metabolic reactions ranging from energy production to the synthesis of vitamin A and prostaglandins and the deoxification and metabolism of drugs, chemicals and foods. Some forms of oxygen and oxygen-containing species are very reactive and can cause significant damage to the organism. Such moieties are termed reactive oxygen species ("ROS").

ROS include hydrogen peroxide, hydroxyl radical, superoxide radical, singlet oxygen, etc. Hydrogen peroxide is relatively stable and remains until it is destroyed or reacts with molecules sensitive to oxidative damage. Other ROS, such as hydroxyl radicals, are very unstable and last no longer than a few picoseconds to seconds, depending on the environment. The hydroxyl radical is one example of another reactive group, referred to as free radical species. Free radicals are atoms, ions or molecules that contain an unpaired free electron. The presence of an unpaired free electron is one of the reasons for the high reactivity and short lifetime of most such species. Free radicals and ROS are normal products of metabolism and are actually involved in the regulation of cellular processes [C. K. Sen and L. Packer, FASEB J., Vol. 10, 227 (1996)]. However, the overproduction of ROS and free radicals is involved in the pathogenesis of a wide variety of human diseases [C. K. Sen and L. Packer, FASEB J., Vol. 10, 227 (1996)]. Such diseases include cancer, diabetes, AIDS, cardiovascular diseases, neurodegenerative diseases, skin diseases, autoimmune diseases and others.

ROS can damage biological macromolecules, cells, tissues and organs in many ways. Oxidation of sulfhydryl groups and other sensitive components of proteins can either increase or decrease the activity of enzymes. It was also recently discovered that oxidative modification of proteins is involved in the control and regulation of many cellular processes [C. K. Sen and L. Packer, FASEB J., Vol. 10, 227 (1996)]. Peroxidation of membrane lipids can result in crosslinking of unsaturated lipids and modification of the cellular permeability to different ions and molecules. Some ions such as calcium are also involved in the control and regulation of cellular processes. Hydroxylation of nucleic acid bases and the breakup of nucleic acids are also deleterious processes that result from the presence of excessive concentrations of ROS. Once formed, many free radicals are involved in "chain reactions" producing other free radicals and ROS. Even the scavenging and degradation of free radicals can produce highly reactive, damaging species. [E. R. Stadtman, Science, Vol. 257, 1220 (1992)].

Organisms, including humans, have evolved ways of handling dangerous ROS. Organisms posses a large number of defenses against the deleterious effects of ROS. [See, for instance, Oxidative Stress, Oxidants and Antioxidants, Academic Press, London, 1991]. Many enzymes and small molecules are used by aerobic cells to protect against the damage caused by ROS. Enzymes which are used to catalyze the removal or transformation of ROS include superoxide dismutase, catalase, glutathione peroxidase, glutathione transferase etc. Small molecules used by aerobic cells to scavenge ROS include vitamins C, E and A, glutathione, ubiquinone, uric acid, carotenoids, etc. Superoxide dismutase is a very efficient catalyst for the removal of superoxide free radicals. Such removal results in the production of hydrogen peroxide. Catalase, in turn, is a very efficient catalyst for the removal of the hydrogen peroxide that is produced. Glutathione peroxidase and transferase enzymes are efficient in the removal of many ROS. Among small molecules, the most important molecule involved in the prevention of damage caused by ROS is a thiol-containing tripeptide, glutathione [see, for instance, Oxidative Stress, Oxidants and Antioxidants, Academic Press, London, 1991]. Glutathione (GSH) is present in all animal cells in millimolar concentrations and is directly involved in the reduction (and, thereby, detoxification) of ROS. Reduction of ROS by glutathione results in oxidation and dimerization of glutathione to the disulfide-linked dimer (GSSG). This oxidized form of glutathione is toxic and oxidizing in itself. Other small molecules such as ascorbate (vitamin C) or tocopherol (vitamin E) also can directly reduce ROS. The difference between enzymes such as superoxide dismutase and small molecules such as vitamin C is that the former can catalytically remove many molecules of ROS, while the latter reacts with oxidants stoichiometrically, usually in a 1:1 or 2:1 ratio.

However, ROS and free radicals are not always toxic. Recent evidence suggests that at moderately high concentrations, certain forms of ROS such as hydrogen peroxide, may act as signal transduction messengers involved in the control of cell proliferation, differentiation and death [C. K. Sen and L. Packer, FASEB J., Vol. 10, 227 (1996)]. Regulation of gene expression by different concentrations of many oxidants and antioxidants has recently been shown. It was shown that the activity of many proteins involved in signal transduction and gene transcription is modified by intracellular redox state [C. K. Sen and L. Packer, FASEB J., Vol. 10, 227 (1996)]. In fact, the regulation of gene expression by oxidants, antioxidants, and the cellular redox state has emerged as a novel subdiscipline in molecular biology that has promising therapeutic implications [C. K. Sen and L. Packer, FASEB J., Vol. 10, 227 (1996)]. Redox-regulated transcription factors such as AP-1 and NFκB have been shown to be implicated in the pathogenesis of many inflammatory diseases, cancer, AIDS, diabetes complications, atherosclerosis and neurodegenerative diseases. It was observed that critical steps in the signal transduction cascades are sensitive to oxidants and antioxidants. It was also shown that the interaction of some membrane proteins, protein phosphorylation and the binding and activation of transcription factors are sensitive to physiological oxidant-antioxidant homeostasis [C. K. Sen and L. Packer, FASEB J., Vol. 10, 227 (1996)]. Sen and Packer suggested those oxidants, antioxidants and other factors that influence intracellular redox status can be developed into novel potential prophylactic and therapeutic agents.

Scientists and other individuals involved in the development of pharmaceutical and dietetic products based on antioxidant action realized the potential usefulness of antioxidants long ago. Many products with potential therapeutic use are described in peer reviewed journals and patent literature. However, those products are currently not completely satisfactory. We will discuss such prior art literature below.

Small molecules are currently used as dietetic supplement antioxidants. Vitamins C and E are probably the most commonly used antioxidant supplements. However, both molecules can easily be oxidized and, when oxidized, become toxic themselves [M. Gabbay et al., Neuropharmacology, Vol. 35, 571 (1996)]. Novel synthetic molecules such as 21-aminosteroids, also termed lazaroids, showed some effect in the prevention of free radical damage to tissue after brain damage but did not show any beneficial effects in clinical trials with stroke patients [RANTTAS Investigators, Stroke, Vol. 27, 195 (1996)]. Lipoic acid and its derivatives have been proposed as therapeutic antioxidants, but those molecules rapidly leave cells and do not sufficiently protect affected tissues from oxidative damage [U.S. Pat. No. 5,728,735]. N-acetyl cysteine (NAC) showed similar positive effects to lipoic acid but it also leaves cells very rapidly [U.S. Pat. No. 5,762,922]. Dithiocarboxylates and ditiocarbamates also showed some promise as therapeutic antioxidants [U.S. Pat. No. 5,821,260]. But at higher concentrations these molecules are toxic. Carotenoids have also showed some limited therapeutic effects in various chronic diseases, including coronary heart diseases, cataract and cancer.

Catalytic antioxidant enzymes have also been tested for their potential therapeutic effects in diseases that are related to the overproduction of free radicals and reactive oxygen species [Uyama et al., Free Radic. Biol. Med., Vol. 8, 265 (1990)]. Superoxide dismutase and catalase showed some therapeutic effects in ROS overproduction related diseases such as stroke, heart attack, and autoimmune diseases such as Crohn's disease and lupus [U.S. Pat. No. 5,834,509, page 6]. The disadvantage of using this approach is that such molecules are large, unstable macromolecules and cannot penetrate in high concentrations to the affected cells and tissues. Moreover, enzymes are proteins and cannot be effectively administered orally. Proteins are digested in the stomach and small intestines and, therefore, most of the catalytic activity is lost. Finally, recombinant proteins are also very expensive.

Small molecules with the catalytic ability to remove superoxide and hydrogen peroxide have recently been synthesized and tested. [U.S. Pat. No. 5,223,538] Such molecules are usually complexes of transition metals such as manganese, copper, zinc, iron or cobalt. Some of the recently tested molecules such as manganese salen complexes [U.S. Pat. No. 5,834,509] even showed catalytic ability to reduce concentrations of both superoxide and hydrogen peroxide. Most of such molecules are either toxic or lack the catalytic ability in-vivo. However, some of the recently tested manganese salen complexes showed low toxicity and reasonable protection against stroke or other tissue degenerative diseases. On the other hand, such molecules cannot scavenge other reactive oxygen species and free radicals such as singlet oxygen, hydroxyl radicals, nitric oxide, peroxynitrite, hypochlorous acid and organic peroxides. [U.S. Pat. No. 5,403,834].

Several other approaches to reduce the toxic effects of ROS and free radicals were tested. Chelating agents were used to prevent the production of very reactive hydroxyl radicals. Such agents bind metals, such as iron or copper, and subsequently prevent the reactions of metal cations with hydrogen peroxide, which yield hydroxyl radicals. Iron chelators and desferroxiamine showed some limited efficiency in the treatment of neurodegenerative diseases. [B. Halliwell, Free Radic. Biol. Med., Vol. 7, 645 (1989)] Unfortunately, at the higher concentrations needed for enhanced activity, such agents are toxic. Spin traps—a class of molecules which are used to trap free radicals to measure free radical concentration, were also used to prevent the tissue damage caused by ROS. [X. Cao and J. W. Phillis, Brain Res., Vol. 644, 267 (1994)] Unfortunately, at the higher concentrations needed for the greater efficiency of such reagents, unacceptable toxicity appears.

SUMMARY OF THE INVENTION

As described in the preceding paragraph, it is clear that more efficient antioxidant agents for prophylactic, therapeutic and industrial uses are needed. Accordingly, an object of the present invention is to provide a novel composition of antioxidants enhanced with stabilized atomic hydrogen having low toxicity. Another object is to provide a method of producing stabilized atomic hydrogen and preparing pharmaceutical and industrial compositions using the stabilized atomic hydrogen. Methods of using such pharmaceutical and industrial compositions and methods of using stabilized atomic hydrogen with other therapeutic agents are also described.

Atomic hydrogen is a reducing free radical consisting of a proton and an electron. It is the second most powerful reducing agent known and it also can release the strongest reducing agent, that is, the free electron [M. Pach and R. Stosser, J. Phys. Chem. A, Vol. 101, 8360 (1997)]. It was recently shown that this very reactive and unstable species can be encaged inside cage-like compounds and become stable for months or even years [R. Sasamori et al., Science, Vol. 265, 1691 (1994)]. In one embodiment of this invention, we describe methods to prepare and stabilize atomic hydrogen photoelectrochemically, electrochemically and plasmachemically. We also describe the use of the most succesful, biomedically acceptable, cage-like compounds, including cobalamin (vitamin B12), potassium silicate and colloidal silicates and aluminosilicates such as zeolites.

In another embodiment of this invention, we describe the preparation of mixtures of stabilized atomic hydrogen with thiol antioxidants, and other highly efficient antioxidants such as polyphenols. Such mixtures are efficient in keeping the concentration of reduced glutathione in cells constant and, subsequently, in preventing oxidative damage to cells.

In yet another embodiment of the invention, it is described how pharmaceutical compositions enhanced with stabilized atomic hydrogen are used to modify gene expression regulation, cell death, proliferation and differentiation for therapeutic purposes.

Furthermore, it is described how pharmaceutical compositions enhanced with the stabilized atomic hydrogen are used in the treatment of cancer, autoimmune diseases such as, diabetes or arthritis, neurological disorders, neurodegenerative diseases, cardiovascular diseases, skin diseases and other disorders which are related to the overproduction of reactive oxygen species and free radicals.

In another embodiment of this invention, we describe how stabilized encaged atomic hydrogen enhanced antioxidants are used to prevent the oxidation of food, industrial oils, plastics and other oxidation-prone materials.

Based on the foregoing, it is clear that more efficient prophylactic and therapeutic antioxidant agents are needed. Such reagents should be of low toxicity, inexpensive to manufacture and store, stable in-vitro and in-vivo, and reactive towards all or most free radicals and reactive oxygen species. Moreover, such agents should be able to penetrate affected cells and tissues and remain there for a prolonged period of time in active form. The ability to penetrate the blood brain barrier would also be a desirable property. The ability to interact with other therapeutic agents without adverse effects would be an important advantage. Finally, the antioxidant agents which can be used to control gene expression regulation and cell proliferation, death or differentiation would be extremely useful therapeutic agents. It is one object of the invention to provide methods to produce and use such a novel class of antioxidants. Such antioxidants could also be used as dietetic supplements. Moreover, such antioxidants could be used to prevent oxidation and free-radical damage in food and in industrial products such as oils and plastics.

As previously mentioned, aerobic organisms on Earth evolved by acquiring the ability to utilize oxygen. However, products of oxygen metabolism, reactive oxygen species, are toxic to most organisms. As also described earlier, evolving organisms developed numerous enzymes such as superoxide dismutase or use small molecules such as vitamin E to scavenge such oxidizing species. It was recently shown that one of the oldest enzymes that can scavenge reactive oxygen species was actually a hydrogenase: an enzyme that splits molecular hydrogen into atomic hydrogen [R. P. Happe et al., Nature, Vol. 385, 126 (1997)]. Atomic hydrogen is a proton plus an electron and is the second most efficient antioxidant after the free electron itself. However, atomic hydrogen can also release free electrons when it encounters powerful oxidants. Unfortunately, atomic hydrogen is also a very reactive species and it disappears within milliseconds of its production.

While some techniques for stabilizing atomic hydrogen have been developed, the atomic hydrogen produced by these techniques can be stabilized only at very low temperatures in solidified noble gas matrices [S. N. Foner et al., J. Chemical Physics, Vol. 32, 963 (1960)]. Recently, Japanese scientists showed that atomic hydrogen can be encaged into cage-like silicates and stabilized at room temperature in solid state and organic solvents for longer than one year [R. Sasamori et al., Science, Vol. 265, 1691 (1994)]. Moreover, mild oxidants such as oxygen, could not scavenge encaged atomic hydrogen, but stronger oxidants caused a release of free electrons. German scientists recently independently confirmed this unusual and important discovery [M. Pach and R. Stosser, J. Phys. Chem. A, Vol. 101, 8360 (1997)]. Shirahata and coworkers showed that the active component of electrochemically-reduced water is also atomic hydrogen, probably encaged into molecular hydrogen bubbles [S. Shirahata et al., Biochem. Biophys. Res. Comm., Vol. 234, 269 (1997)]. However, organic silicates used by German and Japanese scientists to encage atomic hydrogen are toxic, and large amounts of molecular hydrogen used in Shirahata's work are toxic such that they are not suitable for pharmaceutical use.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

Atomic hydrogen can be prepared, electrochemically, photochemically, photo-electrochemically, plasma-chemically, thermally, electromagnetically and with X-ray or gamma-rays, ultrasonically and even with mechanical cavitation. We will describe in more detail three different methods to produce and encage atomic hydrogen. However, this invention incorporates the use of stabilized encaged atomic hydrogen products produced, in addition, by any other methods. Such methods are well known to those skilled in the art.

Electrochemical Method to Produce and Encage Atomic Hydrogen: Electrolysis is a very efficient method of producing atomic hydrogen free electrons. In the past, though, it was not possible to separate oxidizing products produced at the anode and reducing products produced at the cathode. Recently, Japanese scientists used a semipermeable membrane to separate the cathode and anode areas, while not perturbing the flow of electrons delivered to the media. Such devices are, for instance, described in Y. Shiramizu et al., J. Electrochem. Soc., Vol. 143, 1632 (1996), the content of which is incorporated by reference in its entirety. In short, such devices consist of a chamber (usually made of non-corrosive material such as plastic) which is divided in two compartments with a water-tight semipermeable Nafion membrane (Dupont corporation). In each compartment, there is an electrode connected to a DC current source. The electrodes are usually made of platinized titanium in order to be compatible. The electrodes are plates with a large surface area relative to the chamber volume. For a one liter container (500 ml per compartment), the electrodes are ca. 15×10 cm (150 $cm^2$ surface area). Each compartment has a valve that can be opened to empty the device into two separate containers (cathode water and anode water). It was shown by Shirahata and coworkers that such a device can produce atomic hydrogen in the cathode area in S. Shirahata et al., Biochem. Biophys. Res. Comm., Vol. 234, 269 (1997), the content of which is incorporated by reference in its entirety. If cage-like compounds are added to the cathode compartment during electrolysis, atomic hydrogen and/or free electrons can be stabilized and encaged. In one such experiment we added 100 mg of potassium chloride to enhance the conductivity of water to both the cathode and anode water (500 ml each). This brought the concentration of KCl to 200 ppm. Twenty five mg of vitamin B12 (cyanocobalamin) was added to the cathode water to encage the atomic hydrogen/free electrons. This brought the cobalamin concentration to 50 ppm. Other pharmaceutically active components can be added to the cathode area before, or after, electrolysis. Examples of such components will be described later. Several parameters can be measured to ensure the efficiency of electrolysis. The redox potential of the water solution in the cathode area should be at least−700 mV after electrolysis. The pH of water solution in the cathode area after successful electrolysis should be around 11. The efficiency of reduction of vitamin B12 can be tested by measuring UV/VISIBLE spectra and recording the absorbance at 387 nm, which is proportional to the amount of reduced vitamin B12, see G. Chithambarathanu Pillai and E. S. Gould, Inorganic Chemistry, Vol. 25, 3353 (1986), the content of which is incorporated by reference in its entirety. The efficiency of electrolyzed cobalamin solutions as antioxidants can be tested with the standard techniques which will be described later in the text. The efficiency of any stabilized atomic hydrogen solutions in scavenging of superoxide radicals and hydrogen peroxide can be tested as described by Shirahata and coworkers [S. Shirahata et al., Biochem. Biophys. Res. Comm., Vol. 234, 269 (1997)]. The electrolyzed cobalamin solutions should be kept under argon to avoid slow oxidation. The same applies to other cage-like reagents: they should be kept under argon upon electrolysis, and their efficiency as antioxidants should be tested with the standard methods, such as the ability to scavenge superoxide radical in-vitro. If long-term stability of stabilized atomic hydrogen-enhanced products is needed, great care should be taken to remove even minor traces of oxygen from the solution before the product is packaged. In addition, it is easier to encage atomic hydrogen in organic solutions, particularly of aprotic solvents such as dymethyl sulfoxide (DMSO). Non-aqueous solutions of stabilized atomic hydrogen are stable for much longer, up to a year.

Photoelectrochemical Method to Produce and Encage Atomic Hydrogen/Free Electrons: A compact apparatus for photogeneration of hydrated free electrons/atomic hydrogen was described by Schmidt and Hart. To produce free electrons very efficiently, one needs a water solution at pH 11 saturated with molecular hydrogen ($H_2$). Such solutions also have a very low redox potential (lower than −700 mV). See K. Schmidt and E. J. Hart, A Compact Apparatus for Photogeneration of Hydrated Electrons, in Radiation Chemistry—Part I; Aqueous Media, Biology and Dosimetry, ed. E. J. Hart, Advances in Chemistry Series, Vol. 81 (1968); American Chemical Society, Washington, D.C., the content of which is incorporated by reference in its entirety. Such solutions are then irradiated with a pulsed xenon flash lamp at wavelengths between 185 and 230 nm and with at least 100 W of power. Each 40-microsecond pulse produces up to $10^{-7}$ M of free electrons/atomic hydrogen. We modified this process in order to avoid a need for hydrogen gas bottles to sparge the water Instead, we used the electrolysis device described above to produce cathode solutions with pH 11 and low redox potential due to saturation with molecular hydrogen produced at the cathode area. When pH 11 and low redox potential conditions (−700 mV or lower) are reached, one starts irradiation with a pulsed xenon flash lamp, while still performing the electrolysis. Such Photoelectrochemical generation of free electrons/atomic hydrogen is very efficient. It was also realized that longer pulses with a xenon flash lamp (as long as 1 second) can also be efficiently used without overheating the solution. Xenon flash lamps can be submerged into water inside the cathode area of the previously described electrolysis device or kept above the solution. As in the case of the electrolytic production of the atomic hydrogen, cage-like compounds can be added to the water to encage atomic hydrogen. Vitamin B12 at 50 ppm is also used to encage atomic hydrogen/free electrons in such a setting. Other cage-like compounds can be used, as will be described later. Water solutions with encaged atomic hydrogen should be kept under argon to avoid slow oxidation. Other pharmaceutically active components can be added to the water solutions before, or after, the Photoelectrochemical activation.

Plasma—Chemical Method of Producing and Encaging Atomic Hydrogen: Plasma treatment is an ideal method to produce an abundance of free electrons and, if hydrogen is used as a gas, an abundance of atomic hydrogen. Such plasmas are produced in a gas phase such that atomic hydrogen can be delivered to cage-like compounds in both liquid and solid states. In the past, using atomic hydrogen so produced was impossible due to its very short lifetime (milliseconds). Kikuchi and coworkers showed that if a small amount of water vapor is added to the hydrogen plasma, the relative concentration of atomic hydrogen is up to 80 times higher and it becomes stable for long term use. See J. Kikuchi et al., Japanese J. Appl. Phys., Vol. 32, 3120 (1993), the content of which is incorporated by reference in its entirety. Such gaseous atomic hydrogen can then be delivered to both solid-state or liquid-state cage-like compounds. The detailed design of such a plasma device is presented in Kikuchi's paper, referenced above. The water vapor supply is described in S. Fujimura et al., J. Vac. Sci & Technol. B, Vol. 9, 357 (1991), the content of which is incorporated by reference in its entirety. Plasma can be produced with microwaves, radiofrequency, dc current or thermal treatment of the low pressure stream of molecular hydrogen to which water vapor is added. In the preferred embodiment, hydrogen and water vapor are introduced to a quartz tube (9 mm inner diameter) through mass flow controllers. The total gas flow is 100 $cm^3$/min. The total pressure in the quartz tube is 1.0 Torr, as measured with a capacitance manometer. The hydrogen plasma is generated by a microwave generator (2.45 GHz, 20 W power). The dissociated hydrogen flows through the quartz tube and can be used to encage atomic hydrogen up to two meters downstream from the microwave generator. For example, vitamin B12, silica, silicates or zeolites can be used to encage atomic hydrogen. Cage-like reagents can be dissolved in water, organic solvents or can be used as powders. Stabilized atomic hydrogen products should be kept under an argon atmosphere in order to avoid oxidation. The ability of encaged atomic hydrogen to act as an antioxidant can be tested with the standard techniques to be described later [S. Shirahata et al., Biochem. Biophys. Res. Comm., Vol. 234, 269 (1997)]. It should be obvious to the skilled in art that there are many other different ways of producing atomic hydrogen. Such methods are therefore included in this invention.

Pharmaceutically Active Compositions Which Include Stabilized Atomic Hydrogen: The main component of the pharmaceutically active compositions that include stabilized atomic hydrogen is a reagent that is used to encage atomic hydrogen or free electrons. As it was discussed earlier, silicates, particularly those with D4R framework structures, are suitable reagents to encage/stabilize atomic hydrogen. Many natural products have similar cage-like structures. Vitamin B12 (cyanocobalamin) and other cobalamines (e.g. methylcobalamin, hydroxycobalamin, adenosylcobalamin etc.) are very efficient agents to encage free electrons/atomic hydrogen. Chlorophyll is another suitable cage-like substance. Porphyrins, with or without a transition metal inside the cage, are another suitable group of agents to encage free electrons/atomic hydrogen. Salen—mangenese or salen—cobalt complexes [see for instance U.S. Pat. No. 5,834,509] are also suitable cage-like reagents to encage atomic hydrogen/free electrons. Silica, quartz, silicates, aluminosilicates such as zeolites or clays is another group of suitable reagents to encage atomic hydrogen. Those skilled in the art would be able to identify many other suitable cage-like reagents to encage atomic hydrogen. Such reagents are incorporated in this patent.

It has been shown that encaged atomic hydrogen, particularly inside cobalamins, can actually reduce organic disulfides such as glutathione or the oxidized form of lipoic acid. See G. C. Pillai and E. S. Gould, Inorg. Chem., Vol. 25, 3353 (1986), the content of which is incorporated by reference in its entirety. Therefore, it is very useful to add thiol antioxidants to encaged atomic hydrogen, as the second active component. N-acetylcysteine (NAC), lipoic acid, pyrrolidine dithiocarbamate (PDTC) and many other thiol reagents can be used for such purposes. Stabilized atomic hydrogen keeps such reagents in an active—reduced antioxidant form.

Other antioxidants can be added to stabilized atomic hydrogen and thiol reagents. Polyphenols can significantly enhance the efficiency of the stabilized atomic hydrogen—thiol mixtures. Green tea extract, pine bark extract and grape seed extract are very efficient agents for that purpose. Synthetic polyphenols such as catechins can also be used. Other common antioxidants such as vitamin C, E or A can also be added. Those skilled in the art are familiar with many additional antioxidants or electron donors, not mentioned here, which could be added to enhance the performance of stabilized atomic hydrogen. Such antioxidants are therefore included in this patent.

Other pharmaceutically-active agents can be added to the stabilized atomic hydrogen enhanced antioxidants. Anticancer agents, insulin, growth factors, antibodies, cholesterol-lowering agents, pain-relieving agents etc. are only some examples of reagents that can be used to enhance the efficiency of stabilized atomic hydrogen antioxidants. Those skilled in the art are familiar with the pharmaceutically-active components that could be used for such purposes. Examples of diseases or conditions that can be treated with stabilized atomic hydrogen are described later in the text.

Pharmaceutical compositions comprising stabilized encaged atomic hydrogen/free electrons of this invention are useful for oral, topical, transdermal, and parenteral administration (subcutaneous, intravenous or intramuscular). The compositions usually contain between 1 mg/l and 1000 mg/l of cage-like reagents used to encage atomic hydrogen. In addition to water, nontoxic organic solvents (such as DMSO) can be used to dissolve/suspend cage-like reagents before the production of atomic hydrogen/free electrons starts. Single or multiple dosages can be applied on a daily basis. Standard compounding methods described in, for instance, Remington's Pharmaceutical Science, 15th ed., Mack Publishing Company, Easton, Pa. (1980), the content of which is incorporated by reference in its entirety, are used to prepare administrable compositions. Stabilized atomic hydrogen solutions or powders should be kept under argon in order to avoid oxidation. Care should be taken that other active and nonactive ingredients are compatible with the cage-like reagents used to stabilize atomic hydrogen. Great care should be taken to avoid oxygen and carbon dioxide contamination of encaged atomic hydrogen reagents in order to ensure long-term reagent stability.

More efficient delivery of the stabilized atomic hydrogen products deeper into the skin or mucous membranes can be achieved in many ways. Small lipid vesicles known as liposomes can be used as drug carriers. See G. Gregoiraidis, Trends Biotechnol., Vol. 13, pp. 527–537 (1995), the content of which is incorporated by reference in its entirety. Water solutions of cage-like reagents are then encapsulated within the liposome vesicles along with the other active ingredients. Longer-lived liposomes can be produced by attaching a polyethyleneglycol chain. The particle size of the liposome will generally be in the range between 1 and 500 microns. Liposomes can be used for transdermal, parenteral or oral delivery. Numerous stimuli can be used to enhance the transdermal transport, such as ultrasound, electromagnetism, electricity or plasma pulses. See R. Langer, Nature, Vol. 392, suppl., pp. 5–10 (1998), the content of which is incorporated by reference in its entirety. Such stimuli can, for instance, be applied directly at the spot where acne, skin cancer or psoriasis lesions are present in order to enhance the delivery of cage-like reagents with other medications.

Examples Of Research Results On The Activity Of Encaged Atomic Hydrogen: The following are examples of research results that provide a proof of the efficiency and mechanism of the action of encaged atomic hydrogen-enhanced products. Generally, for in-vivo experiments, stabilized atomic hydrogen-enhanced antioxidants were prepared by 12 minutes of membrane electrolysis (800 mA, 12 V) utilizing cathode solutions containing 200 ppm of KCl, 50 ppm of cyanocobalamin, 500 ppm of N-acetylcysteine and 500 ppm of standardized green tea extract (250 ppm of pure polyphenols). Only 200 ppm of KCl was added to the anode water (500 ml of water solution used). Human subjects were allowed to drink 500 ml of such solution collected from the cathode area per day. Animals had free access to such water solutions. General Antioxidant Action: Standardized tests showed that electrochemically-produced atomic hydrogen (12 minute electrolysis of 100 ppm of KCl) can, even on its own and without the presence of other antioxidants, scavenge super oxide, hydroxyl radicals, singlet oxygen, nitric oxide and peroxynitrite. If cage-like agents, such as vitamin B12, are added to the solution before electrolysis, the scavenging ability of the electrolyzed solution is enhanced in a dose-dependent fashion. These results were independently confirmed by other researchers [S. Shirahata et al., Biochem. Biophys. Res. Comm., Vol. 234, 269 (1997)]. In vitro tissue culture experiments with human dermal fibroblasts cultures and other commonly used cell cultures showed that stabilized atomic hydrogen can prevent oxidative damage to tissue, DNA, proteins and lipids. Standard assays were used, such as DNA fragmentation measurements, protein carbonyl measurements or TBARs (oxidized lipids)measurements. It was also shown that when stabilized atomic hydrogen is added to cells with additional thiol antioxidants, such as N-acetyl cysteine, the amount of reduced gluthatione in cells can be kept nearly constant, even when oxidants are present. Such findings are, in vitro, independently confirmed. [J. H. Zagal et al., J. Electroanal. Chem. , Vol. 374, 215 (1994)] It was also shown that the addition of stabilized atomic hydrogen can prevent apoptosis of human dermal fibroblasts caused by the addition of various free radicals and reactive oxygen species such as hydrogen peroxide, hydroxyl radicals or peroxynitrite.

Oncology Applications: Antioxidants, if strong enough, have potential applications in three oncology areas: 1) to reduce side effects of radiation and chemotherapy; 2) to help kill cancer cells or to stop their proliferation; and 3) to help reduce or eliminate drug resistance in cancer cells. The collected results show great promise of atomic hydrogen-enhanced antioxidants in all of the above-mentioned applications. A synergistic application with other pharmaceutically active products in all three applications would be advantageous. The following illustrates this potential:

1) to reduce side effects of chemotherapy or radiation: The application of stabilized atomic hydrogen-based antioxidants has been shown to reduce apoptosis of numerous cell types in tissue culture experiments. In these experiments, apoptosis was caused by chemotherapeutic agents, such as etoposide, doxorubicin or cis-platin. We have also worked with a number of patients who were treated with cis-platin—etoposide and later with cyclophosphamide-adriamycin-vincrestine, for lung cancer treatment. Excellent results were observed in the protection of blood vessels, heart cells and blood cells. Unfortunately, we could not fully protect patients from neuropathies caused by vincrestine. Synergism with other pharmaceutically products in this arena could produce better results. Our product was delivered orally, as a liquid. Only non-toxic drugs were used to encage atomic hydrogen. Preliminary toxicity tests show that atomic hydrogen did not change the toxicology of the ingredient chemicals, which are all FDA-approved.

2) to help kill cancer cells or to stop their proliferation: In vitro experiments with numerous cancer cell lines, such as adenocarcinoma A549 or osteosarcoma, indicate that powerful atomic hydrogen-based antioxidants can slow their proliferation. Such experiments with other antioxidants, performed by other scientists, show similar results [S. Shirahata et al., Paper presented at the 10th Annual Meeting of Japanese Association for Animal Cell Technology, Nagoya, Nov. 5–8 (1997); J. M. Turley et al., Cell Growth Differ., Vol. 6, 655 (1995)]. We have worked with several terminal patients, dying from metastatic adenocarcinomas of the lung. In several cases, tumor growth rate was significantly slowed, even in the late stages of the disease. Molecular studies with adenocarcinoma A549 cells show that we significantly reduced the activation of protein kinase JNK-1 and, to a lesser extent, ERK-1, and also the activation of AP-1 transcription factor. Activation of JNK-1 has recently been implicated in the growth of adenocarcinoma cells [ F. Bost et al., J. Biol. Chem., Vol. 272:, 33422 (1997)].

We also showed that the addition of atomic hydrogen-enhanced antioxidants helps to enhance the activity of chemotherapeutic agents in killing adenocarcinoma cells of lung or colorectal cancer. Such action of strong antioxidants has recently been described by other researchers [R. Chinery et al., Nature Medicine, Vol. 3, 1233 (1997)]. The molecular mechanism of such action was also studied: numerous human cancers have a mutation in the p53 tumor suppressor gene. Molecular studies show that antioxidants activate another tumor suppressor molecule, $p21^{WAF1/CIP1}$ in p53-independent way. The mechanism of activation also involves the transcription factor C/EPBβ. This activation seems to occur through activation of the protein kinase A [R. Chinery et al., Nature Medicine, Vol. 3, 1233 (1997).; R. Chinery et al., J. Biol. Chem., Vol. 272, 30356 (1997).; F. Raymond et al., Free Radic. Biol. Med., Vol. 22, 623 (1997)].

We also see a significant increase in the amount of the IL-6 protein and its m-RNA. The activation of NF-IL-6 transcription factor also occurs. We have also worked with several limited stage, small cell lung carcinoma patients and the chemotherapeutic treatment of their tumors. Drinking one of the stabilized atomic hydrogen enhanced antioxidants products essentially destroyed the tumor, up to 1 cm in diameter, after four rounds of chemotherapy. In a one year period, metastatic tumors have not reappeared in these patients.

3) to help reduce or eliminate drug resistance in cancer cells: Most tumors respond well to chemotherapy in the beginning. Unfortunately, during extended treatment, cancer cells become resistant to drugs and metastatic growth follows shortly thereafter, resulting in death or serious suffering. It was recently realized that stress activated protein kinases, such as JNK-1 and other kinases, such as JAK's, are involved in the development of drug resistance [A. Levitzki, Paper presented at the 1st International Conference on Signal Transduction, Dubrovnik, Croatia, Oct. 8–11 (1998)]. As mentioned before, stabilized atomic hydrogen can deactivate JNK-1. Preliminary results indicate that the time of the onset of drug resistance can be delayed by these agents.

Auto Immune Diseases: Free radicals and reactive oxygen and nitrogen species have been implicated in the mechanisms of action of both B and T cells [C. K. Sen and L. Packer, FASEB J., Vol. 10, 227 (1996)]. Reactive oxygen species are also implicated as chemoattractants for numerous lymphocytes. Many highly pro-inflammatory cytokines and chemokines, such as TNFα, IL-1 or IL-8, promote inflammatory cascades through production of reactive oxygen and nitrogen species. Down-regulating or reducing the production or local levels of reactive oxygen and nitrogen species can down regulate the activation and action of the immune system. Such deactivation is desirable in numerous auto immune diseases. Through in-vitro testing, we have observed that stabilized atomic hydrogen enhanced antioxidants can scavenge both oxygen and nitrogen free radicals and other reactive species. Such scavenging of both oxygen and nitrogen species appears to aid in the deactivation of macrophages, neutrophils and T cells. In tissue culture experiments, we notice a slowed proliferation of macrophages, neutrophils and Wurzburg cells. Also demonstrated experimentally is the inhibition of the inducible activation of the transcription factor NFκB, which is involved in many inflammatory processes. We have shown prevention of TNFα promoted apoptosis of several different cell lines. There are indications that atomic hydrogen-rich water can, to some extent, inhibit gene expression of cyclooxygenase 2 (COX2) and lypooxygenase enzymes, which are involved in pro-inflammatory signal transduction cascades.

Through in-vivo work with human patients and laboratory animals, we have conducted research on both insulin-dependent and adult onset diabetes mellitus. It was observed that stabilized atomic hydrogen rich antioxidants decreased such complications as deteriorating eyesight, open wounds and other polyneuropathies. A decrease in the concentration of glucose in the blood occurred with most patients after three to six months of treatment. In work with non-obese diabetic (NOD) mice, our preliminary results show that we can significantly inhibit the onset of disease. We know that these agents inhibit the activation of the JNK-1 molecule in many cell types. It was recently reported in Science, that JNK-1 deficient mice show problems with differentiation of the immune system: no Th1 helper CD4 cells were formed; instead, Th2 cells prevailed [C. Dong et al., Science, Vol. 282, 2092 (1998)]. It was also recently shown that, at least in the mouse model, one can prevent the onset of diabetes, if Th2, rather than Th1 CD4, cells are present [K. Bellman et al., Int. J. Immunopharmac., Vol. 19, 573 (1997)]. This change in the type of differentiated Th cells is associated with the increased nuclear accumulation of NFATc transcription factor. It was also shown that stabilized atomic hydrogen enhanced antioxidants can scavenge peroxynitrite, which was implicated in the damage to pancreatic β cells and the progression of diabetes, as well as diabetic complications.

Neurological Disorders: In tissue culture experiments, we have found that atomic hydrogen rich products can prevent apoptosis of neurons. Apoptosis inducing agents tested include dopamine, hydrogen peroxide, hydroxyl radicals, peroxynitrite and removal of growth factors. It is also found that encaged atomic hydrogen products may combine synergistically with growth factors further reducing apoptosis. Preliminary in-vivo results with apoptosis caused by ischemia-reperfusion, also show significant decrease in the size of infarction and in the amount of cell death. Some work with ALS and Parkinson's patients shows that these products reduce treatment related side effects. In the ALS case, two young female patients did not show development of new lesions after one year of using atomic hydrogen rich water.

It was also observed that routine drinking of atomic hydrogen rich water is associated with weight loss and appetite diminishment using 20 young, healthy volunteers. The resulting weight loss of between 5 and 35 pounds was registered after six months of use. Several heavy smokers also reported a significant reduction in craving for cigarettes after drinking the enriched water for about one month. This result warrants more research.

Skin and Mucous Membrane Care Applications: Oxidative damage to skin is implicated in skin aging and wrinkling, and is also involved in the initiation of skin cancer lesions. As mentioned earlier, it was shown that oxidative attack on fibroblasts grown in cell cultures can be prevented with the atomic hydrogen rich products. Oxidative damage to fibroblasts used in such experiments is caused with the UVA and UVB rays, singlet oxygen donors, nitric oxide donors (SNAP), peroxynitrite donors (SIN-1) etc. Apoptosis (cell death) of fibroblats is significantly (up to 85%) reduced in the presence of atomic hydrogen enriched antioxidants in a dose dependent manner. Activation of pro-inflammatory transcription factors AP-1 and NFκB is also prevented. In addition, oxidation of lipids, proteins and DNA is significantly reduced. This results in significant inhibition of activation of metalloproteinases and VCAM-1 adhesion molecules which are involved in the skin aging process and potential carcinogenesis. Similar products can also be used in oral care and in the treatment of psoriasis. Standard methods used in the prior art were used to perform such experiments (for instance, methods described in "Methods in Enzymology" series).

Cardiovascular Diseases: As mentioned previously, we found that the application of atomic hydrogen rich products in-vitro and in-vivo prevented oxidative damage to lipids, lipoproteins and DNAIt was also shown that stabilized atomic hydrogen enhanced antioxidants inhibit the activation of JNK-1 protein kinase. Additionally, activation of transcription factors NFκB, AP-1 and ATF was inhibited. This inhibition prevented activation of metalloproteinases and VCAM-1 adhesion molecules. All of the above mentioned activities are beneficial in the prevention and treatment of arteriosclerosis and other cardiovascular diseases. [Th. Force et al., Circ. Res., Vol. 78, 947 (1996).] In-vivo experiments with New Zealand white rabbits that were fed cholesterol rich food showed that drinking of atomic hydrogen rich water significantly reduced deposit formation in the arteries. Preliminary results with human volunteers showed the improvement in cardiovascular performance and the reduction in thickness of arterial plaque.

Industrial Applications of Stabilized Atomic Hydrogen: Many food products, oils and waxes, hydrocarbons, rubbers, petroleum chemicals, polymerizable resins, adhesives, polymer precursors, sealants and similar materials are sensitive to oxidation mediated undesired changes such as food spoilage, oxidative decomposition or oxidative polymerization. Antioxidants can prevent such undesirable changes by scavenging free radicals and other reactive oxygen species. [U.S. Pat. No. 5,834,509, page 8 for instance] Stabilized atomic hydrogen can be efficiently used to prevent such undesirable oxidative changes. Cage-like compounds used and active compositions are similar to those applied for pharmaceutical purposes. Those skilled in the art will be familiar with the methods how to use and test the efficiency of stabilized atomic hydrogen enhanced antioxidants for such purposes.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A pharmaceutical solution consisting essentially of (i) an antioxidant effective amount of encaged atomic hydrogen in a cage-like compound, wherein the cage-like compound is present in the solution between 1 mg/l and 1,000 mg/l, and wherein the cage-like compound is selected from the group consisting of cobalamines, vitamin $B_{12}$, chlorophyll, porphyrins, salen-manganese complexes, salen-cobalt complexes, silica, quartz, silicates, aluminosilicates, zeolites and clays, and (ii) an atomic hydrogen-stabilizing effective amount of an antioxidant compound.

2. The pharmaceutical solution of claim 1, wherein the antioxidant compound in (ii) is a thiol antioxidant compound.

3. The pharmaceutical solution of claim 2, further containing a polyphenol antioxidant compound.

* * * * *